(12) United States Patent
Booth

(10) Patent No.: US 7,502,694 B2
(45) Date of Patent: Mar. 10, 2009

(54) SONIC EXCITER

(76) Inventor: Galt B. Booth, 44 Bristol St., Branford, CT (US) 06405

( * ) Notice: Subject to any disclaimer, the term of this patent is extended or adjusted under 35 U.S.C. 154(b) by 468 days.

(21) Appl. No.: 11/245,971

(22) Filed: Oct. 6, 2005

(65) Prior Publication Data

US 2006/0078131 A1 Apr. 13, 2006

Related U.S. Application Data

(60) Provisional application No. 60/617,143, filed on Oct. 7, 2004.

(51) Int. Cl.
*G01B 5/28* (2006.01)
(52) U.S. Cl. ...................................................... 702/39
(58) Field of Classification Search ................... 702/34, 702/39, 56, 171, 172; 73/602
See application file for complete search history.

(56) References Cited

U.S. PATENT DOCUMENTS

| | | | | |
|---|---|---|---|---|
| 5,942,736 A | * | 8/1999 | Cortonesi | 181/289 |
| 6,443,586 B1 | * | 9/2002 | Azima et al. | 362/86 |
| 6,669,553 B2 | * | 12/2003 | Adams | 454/237 |
| 6,728,661 B1 | | 4/2004 | Cannelli et al. | |

OTHER PUBLICATIONS

Joseph Vignola et al., Proper Orthogonal Decomposition Analysis of Scanning Laser Doppler Vibrometer Measurements of Plaster Status at the US Capitol, Sixth International Conference on Vibration Measurements by Laser Techniques, 2004, pp. 358-366, Proc. of SPIE vol. 5503, Bellingham, WA.

* cited by examiner

*Primary Examiner*—Bryan Bui
(74) *Attorney, Agent, or Firm*—Bachman & LaPointe, P.C.

(57) ABSTRACT

An apparatus for sonic excitation of a surface includes a transparent pane. A sidewall structure cooperates with the pane to define an open cavity facing the surface. At least one speaker is positioned to introduce sound to the cavity. Sound cancellation may be provided for at least partially canceling transmission of the sound outside the cavity.

20 Claims, 5 Drawing Sheets

SONIC EXCITER

CROSS-REFERENCE TO RELATED APPLICATION

Benefit is claimed of U.S. Patent Application Ser. No. 60/617,143, filed Oct. 7, 2004, and entitled "Sonic Exciter", the disclosure of which is incorporated by reference herein as if set forth at length.

BACKGROUND OF THE INVENTION

The invention relates to art conservation. More particularly, the invention relates to sonic systems for determining the condition of frescos and similar murals.

A fresco mural (e.g., painting or mosaic) is a painting made on a masonry wall by brushing pigment-water mixtures into a fresh plaster layer, or by inlaying small pieces of colored glass, stones, or other materials into a fresh plaster layer. Fresco murals have endured thousands of years.

The interiors of the U.S. Capitol buildings have many fresco paintings, each over 100 years old, many in need of substrate repair. See, Barbara A. Wolanin, "Constantino Brumidi: Artist of the Capitol" (U.S. Government Printing Office, Washington, D.C., 1998). A similar situation exists in buildings of the Vatican and in other Italian locations and other locations near the Mediterranean Sea.

An exploratory technique has been used to evaluate fresco substrates by using a loudspeaker system to direct sound waves toward the fresco mural and a laser interferometer vibration sensor to measure the resulting motion of many locations of the mural. A sound pressure level of 90 to 100 dB is needed to obtain enough motion to measure, but makes the location near the painting too noisy for normal use. See, J. Vignola, J. Bucaro, J. Tressler, D. Ellingston, A. Kurdila, G. Adams, B. Marchetti, A. Agnani, E. Esposito, E. P. Thomasini, "Proper Orthogonal Decomposition Analysis of Scanning Laser Doppler Vibrometer Measurements of Plaster Status at the US Capitol", 6th Int. Conf. on Vibration Measurements by Laser Techniques, Proc. SPIE Vol 5503. See, also, U.S. Pat. No. 6,728,661 of Cannelli et al., identifying use of a wideband acoustic detector.

BRIEF SUMMARY OF THE INVENTION

The present invention provides a sonic exciter which may be used in combination with one or more existing or yet-developed detectors (e.g., vibration sensing systems), components, and protocols. Contrasted with certain systems utilizing relatively remote and/or relatively exposed sound sources (potentially damaging to the hearing of people nearby), the present exciter may provide a relatively low level of sound within the room outside a cavity defined by the exciter. This may involve various measures for blocking leakage of sound and/or passive or active sound canceling techniques.

The exemplary sonic exciter provides a non-contact sound source with adjustable or selectable feet and a sound cancellation feature used to locate faults below the surface of a fresco mural.

The exemplary sonic exciter looks something like a heavy duty picture frame. The following text assumes that the large fresco painting to be studied is on a vertical wall of a room. The sonic exciter has a frame, typically, but not necessarily, rectangular, surrounding a work area, typically 30 inches by 60 inches in area. External supports are provided to hold the frame so that the soft feet on the painting side of the frame, typically of wood or other soft material unlikely to damage the painting in an accidental contact, are about 0.5 to 1.0 cm away from, but not touching, the fresco painting. The cross-sections of the arms of the frame typically are also rectangular, with loudspeakers mounted on each of the inner frame surfaces, directed inward, parallel to the wall, into the volume beside the work area. A window, through which laser beams can pass, is mounted to the room side of the frame. Around the outside of the frame, near the wood feet, are many adjustable sound canceling openings connecting the inside of the frame to the room.

The loudspeakers of the exemplary sonic exciter are driven by a sonic exciter driver, typically in the 50 to 1000 Hz frequency range. The sonic exciter driver includes a powerful audio amplifier with series resistor outputs for each of the loudspeakers of the sonic exciter. Since the loudspeakers have a very reactive load, and cannot radiate energy as they normally do, these resistors are provided to prevent the loudspeakers, and the amplifier, from failing due to overheating. These resistors provide an additional function of damping the major acoustic resonances of the volume beside the work area. Also provided are circuits to set the frequency, amplitude, and duration of the sonic pulses. The sonic pulse does not occur if such settings would produce a calculated excess of projected loudspeaker coil displacement, and/or a projected excess of the temperatures of the loudspeaker coil and/or of the amplifier.

For a flat wall, as described above, the wood feet are thin and flat, covering the entire fresco side of the frame. If, however, the fresco mural is on a curved wall, such as a cylindrical ceiling of a corridor, the flat feet are removed and replaced by thicker feet having curved surfaces toward the painting, shaped to be near but not touching, the painting surface, to minimize the amount of escaping sound.

With the sound cancellation off, and a sound pressure in the volume above the work area of 90 dB, the sound escaping from the gap/slot between the wood feet and the painting typically would cause a room sound pressure level of about 60 dB about 3 meters (11 feet) from the frame. Controls are provided on the frame to provide a canceling sound through the openings to reduce the room sound pressure level by 10 to 15 dB to about 45 to 50 dB, still very audible, but low enough so normal speech can be understood.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
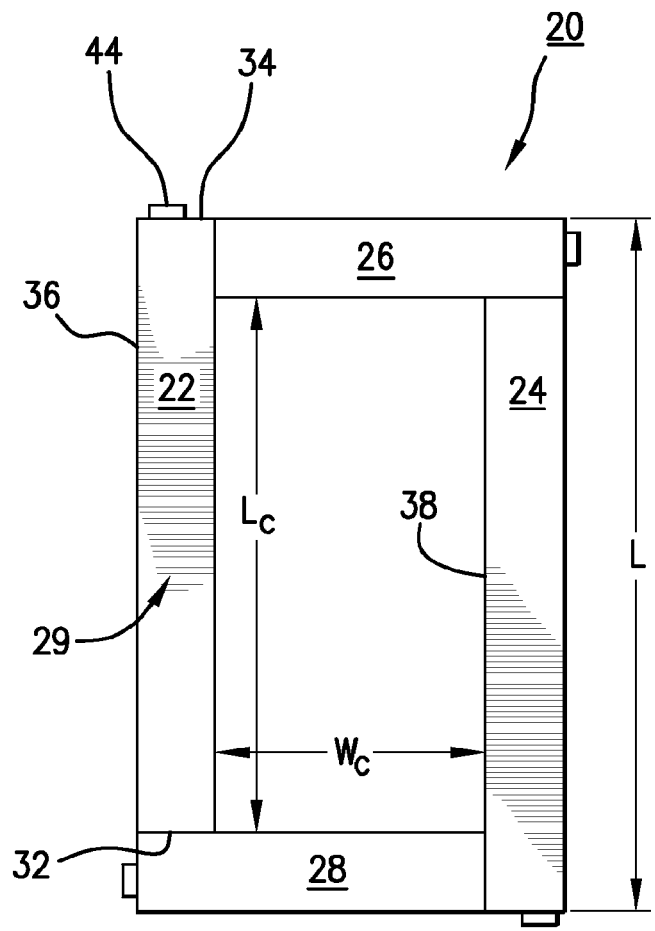
FIG. 1 is a plan view of a first exciter.
Figure 2:
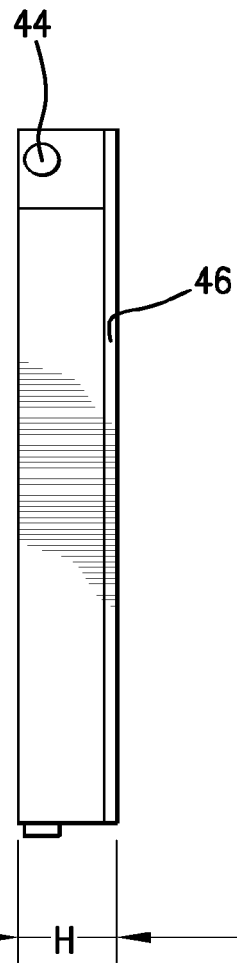
FIG. 2 is a side view of the exciter of FIG. 1.
Figure 3:
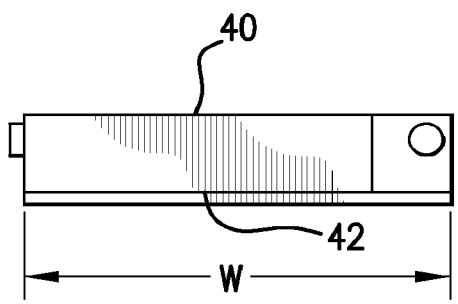
FIG. 3 is an end view of the exciter of FIG. 1.

FIGS. 1-3 show one example of a sonic exciter 20. The exemplary exciter 20 has four hollow arm-like housing components 22, 24, 26, and 28. The exemplary arms are generally straight and positioned end-to-end at right angles to form a generally rectangular frame or wall structure 29 surrounding a central chamber or cavity 30. Each of the exemplary arms has a first end 32, a second end 34, an outboard side 36, an inboard side 38, a top 40, and a bottom 42.

In the exemplary non-square rectangular exciter, the longer cavity dimension is identified as a length $L_C$ while the shorter cavity dimension is identified as a width $W_C$. Overall nominal width, length, and height are shown as W, L, and H (ignoring any protruding adjustment knob 44 (discussed below) or other similar structure (e.g., switches, connectors, and the like). Exemplary $L_C$ is 60 inches (1.5 m), $W_C$ is 30 inches (0.76 m), L is 76 inches (1.9 m), W is 46 inches (1.2 m), and H is 8 inches (0.2 m). Exemplary ranges of lengths and widths are 0.1-2.5 m, depending upon intended use. Exemplary heights are 0.1-0.3 m.

As is discussed below, the structure of the arms may be formed from a relatively rigid and strong material. It may be desired to provide a protective material to prevent any structural material from damaging the mural in the event of intentional or accidental contact. Accordingly, the exemplary embodiment includes a foot or base material 46 secured to the assembled bottoms 42 to surround the cavity 30 (e.g., either as a single continuous piece or as separate pieces for each arm or side of the frame). Exemplary base material is lightweight and has a low adhesion to the mural paint (e.g., in case of an accidental contact). The base material may be removable and replaceable (e.g., to permit installation of base components shaped to accommodate desired shapes of mural surfaces). Exemplary attachment is by fasteners such as screws. Exemplary materials include soft woods and cellular plastics (e.g., cellular polyvinylchloride (PVC) such as is available under the trademark AVEK from AVEK Trimboards of Moosic, Pa. Such material may be particularly useful for applications where the exciter is intended as a non-contact device and there may be light accidental contact. A substantially more compliant material may be appropriate for contact use (e.g., a flexible polymeric foam such as polyurethane). Although the illustrated base material covers substantially an entirety of the undersides of the arm structures, other configurations are possible (e.g., along only a perimeter portion).

Figure 4:
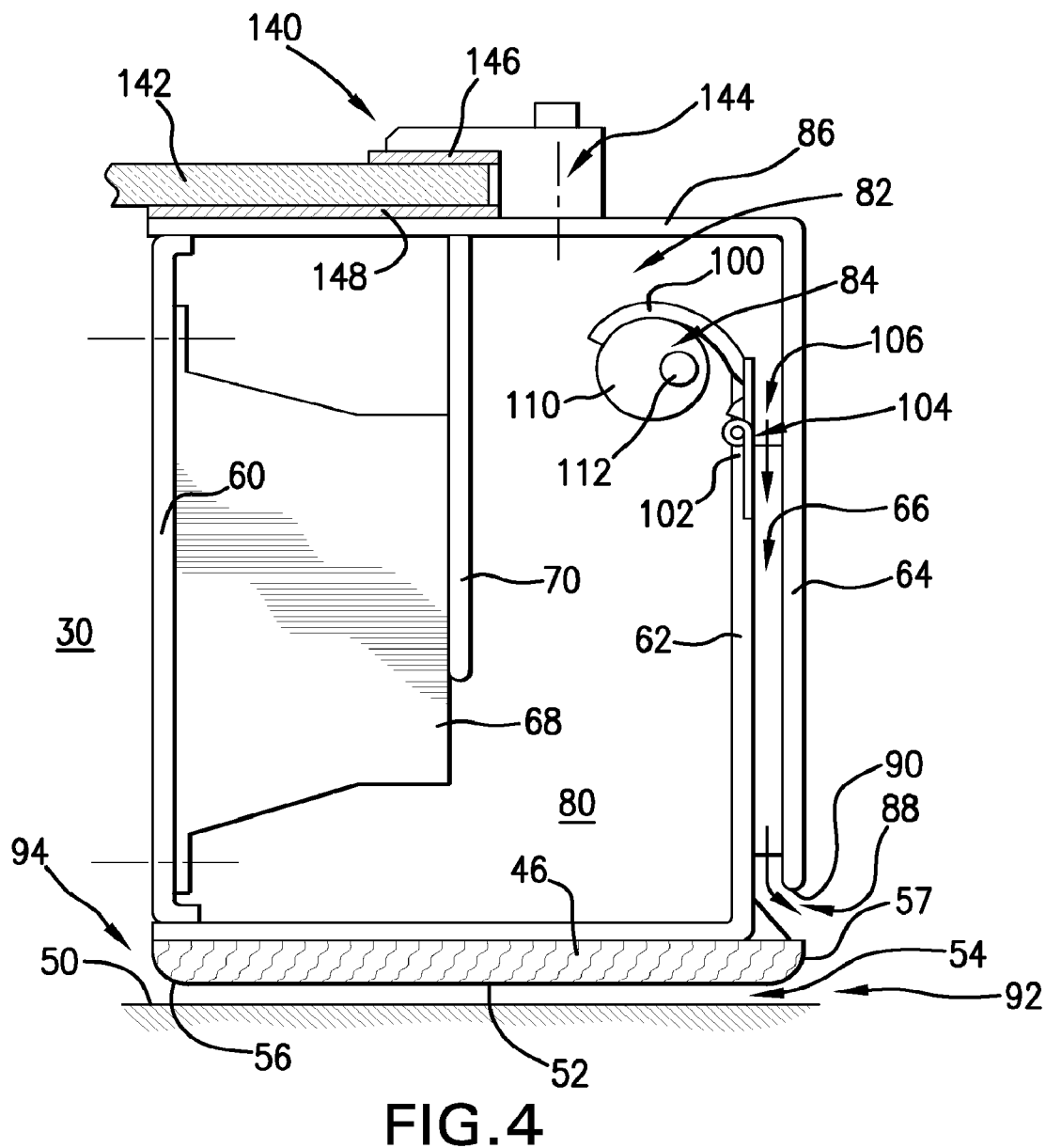
FIG. 4 is a cross-sectional view of a side of the exciter of FIG. 1.

FIG. 4 shows further details of an exemplary arm with the exciter held adjacent a surface 50 of a mural with an underside 52 of the base 46 spaced apart from the mural by a gap 54. Inboard and outboard edges 56 and 57 of the underside 52 may be radiused or otherwise convexly curved to reduce chances of damage to the mural by accidental contact. Exemplary gaps are 5-10 mm in height. The exemplary arm structure has a single layer inner/inboard wall 60 and a generally double layered outer/outboard wall having an inner layer 62 and an outer layer 64 with air passageway 66 therebetween. A loudspeaker 68 is shown positioned facing the cavity 30 with its flange mounted to the inner wall 60 and its magnet supported by an internal brace structure 70 of the arm. The inner wall may include vent openings in front of the speakers to permit sound passage into the cavity 30. There may be multiple loudspeakers arrayed along the length of each arm. Especially with a metallic arm structure, the internal brace member 70 may help conduct heat from the speaker in addition to providing structural support.

The exemplary materials for the arm structure include metals (e.g., aluminum alloys), woods, and plastics (e.g., cellular polyvinyl chloride). The arm has a main interior volume 80. An inlet 82 from the main volume 80 to the passageway 66 is formed by a valve assembly 84 cooperating with an upper wall 86. An outlet 88 is formed below a bottom edge 90 of the outer wall layer 64 in close proximity to an exterior/outboard perimeter 92 of the gap 54.

In operation and as discussed further below, the speakers 68 direct sound to the cavity 30. Some of this sound enters the gap 54 at an inboard perimeter 94 thereof and exits at the outboard perimeter 92. Sound is also produced in the volume 80 of each arm which forms a backspace of the associated speakers. Sound waves from the main volume 80 may pass through the passageway 66 and exit the outlet 88. By appropriate dimensional selections and adjustment of the valve 84, sound exiting the passageway 66 may at least partially cancel sound exiting the gap 54. The level of sound experienced by operators and others in the room may thus be limited by use of this sound cancellation. The exemplary valve 84 includes an arcuate inlet sheet member 100 mounted to an outboard end portion 102 of the inner wall layer 62 by a hinge structure 104. Rotation of the member 100 about the hinge axis may simultaneously vary the size of a collection area defined at the inlet 82 and the size of a throat area 106 at an intermediate location along the member 100 outboard of the hinge. Actuation may be achieved by a manually-controlled or automatically-controlled actuator. An exemplary manually-controlled actuator features an eccentric driven cam 110 contacting a concave surface of the member 100. The cam 110 is mounted on an axle shaft 112 mounted in the arm for rotation about its central longitudinal axis. An end of the shaft may be connected to the associated knob 44. The member 100 may be held against the cam by a biasing spring (not shown). An exemplary material for the member 100 is a high temperature plastic such as chlorinated polyvinyl chloride (CPVC).

Figure 5:
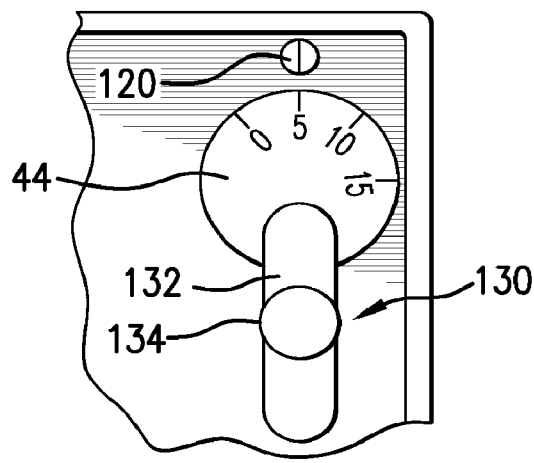
FIG. 5 is an end view of a side of the exciter of FIG. 1.

FIG. 5 shows the knob 44 as bearing index indicia (e.g., numerical) which may register with a reference indicator 120 (e.g., an index post). The indicia may, for example, be selected to represent a characteristic gap height along that associated side. Accordingly, at least an initial adjustment may be made by measuring the gap height and adjusting the knob to the associated height for each arm. Further fine tuning could be performed via feedback. The knob may be provided with a detent mechanism, friction mechanism, and/or a locking mechanism. An exemplary friction locking mechanism comprises a friction clamp arm 130 having a friction under surface 132 and a handle 134 that may be used to tighten the friction clamp arm against the knob face to lock the knob after fine tuning.

FIG. 4 further shows a cover plate assembly 140 having a transparent plate or window pane 142. Exemplary material for the pane 142 is glass, transparent polymer, or combinations thereof. An exemplary transparent polymer is polycarbonate which has advantages of light weight and shatter resistance. An exemplary thickness for a polycarbonate pane is 12-19 mm. The exemplary pane 42 may be mounted to the outboard wall 86 such as by clamps 144 and rubber or other resilient gaskets 146 and 148, or within the cavity 30 by other means. The pane may have an anti-reflection coating on one or both faces.

Figure 6:
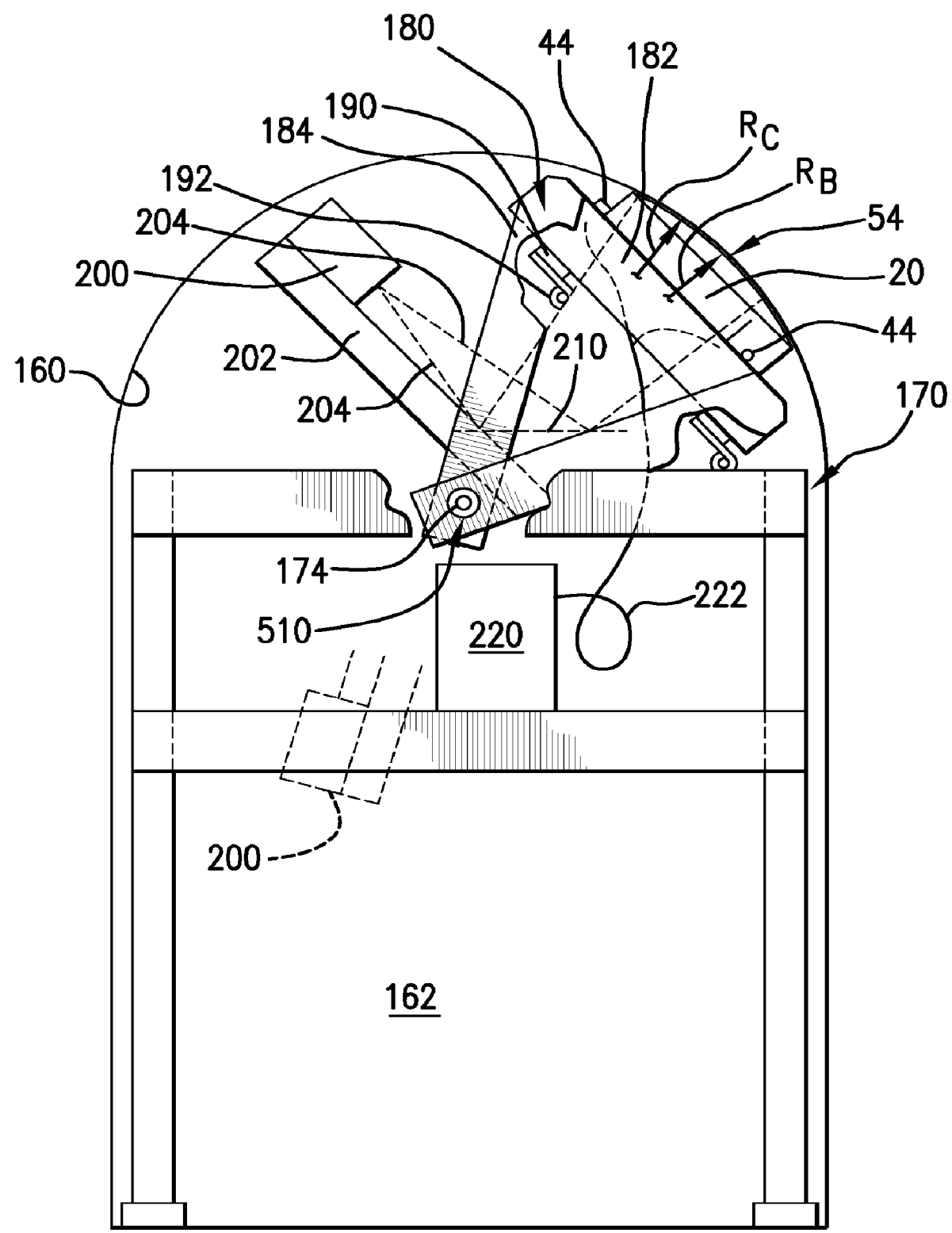
FIG. 6 is a view of the exciter of FIG. 1 positioned for surveying a corridor.

FIG. 6 shows the exciter 20 positioned to examine a fresco 160 on the semi-cylindrical ceiling of a corridor 162. An exemplary corridor is 12 feet (3.7 m) wide for a ceiling height of 18 feet (5.5 m). A scaffold-like or other support structure 170 is assembled within the corridor and may include a work platform 172. The structure 170 may support an axle shaft 174 having an axis 510 at the center of curvature of the ceiling.

An exciter carrier 180 is pivotally mounted to the axle 174 for rotation about the axis 510. The exemplary carrier 180 includes a centrally apertured frame 182 held on pivot arms 184. The frame 182 carries mounting jacks 190 which have adjustable driving portions (e.g., handles 192 and jack screws) and driven portions (e.g., screw followers) (not shown). The driven portions are engaged to the exciter 20 to permit positional adjustments of the exciter 20 to minimize the gap 54. In the exemplary implementation for curved surface, the base may have a curvature complementary to a local curvature of the ceiling. In the exemplary implementation, along the short sides of the assembled exciter, the base has a convex curvature $R_B$ nearly identical to a concave curvature $R_C$ of the ceiling. If the ceiling surface is singly concave along the long side, the base may have substantially no end-to-end curvature. For a doubly concave (e.g., domed) surface, the bases on all sides may be chosen for complementary curvature.

FIG. 6 further shows a laser generator and detector/sensor unit 200 carried at the end of an additional arm 202 of the carrier 180. The laser may be scannable over essentially the entirety of the pane covering the cavity. In the exemplary embodiment, the perimeter of the scanning field is shown as 204. Although the exemplary unit 200 may be positioned directly in front of the pane, to achieve a desired scanning range without interference from the axle it is off-center, with the beam and view reflected by a mirror 210. Although shown as a flat mirror, a convex mirror may be used to further augment the effective field of view. FIG. 6 also shows a driver unit 220 which may be connected to the exciter housing by means of cables 222. In an automated system, the driver 220 and unit 200 may each be connected to a controller (not shown). The cables are coupled to the speakers to drive the speakers and may be configured to permit individual control of individual speakers or groups of speakers or may be configured to drive all the speakers in common.

In operation, after the scaffolding and exciter unit have been installed, the unit may be tuned in a first position. With the speakers being driven, the laser may scan across the area of the cavity. The detector receives laser light reflected from the surface of the mural. Depending upon subsurface condition, the mural surface will vibrate responsive to the sound. This vibration will affect the character of the reflected light. A preliminary laser scan may be made, including the coordinates of all of the intended test locations (points) within the field of view. This preliminary scan makes ensures that an adequate reflected signal is obtained at each point. A complex combination of factors including the paint topography and particular beam path to/from the point may prevent receipt of an adequate reflected signal. Even a slight repositioning of the exciter may cure this. For tuning, a low level sound may be generated, and each of the four sound cancellation knobs 44 may be adjusted for a minimum sound level (e.g., measured by ear or microphone adjacent the associated arm) The knobs may then be locked. Next, the higher volume desired sound excitation may be applied and the data taken at each of one-to all points in the scan and saved. If large surface velocities or displacements are present in an area, a fault below the surface is likely to exist in such area. Any of several known or yet-developed techniques may be used to determine the character, depth, and extent of any subsurface defect based upon the detected light. Depending on the particular protocol used, in a given position, there may be multiple scans (e.g., at different sound frequencies). Exemplary sound frequencies are in the range of 50-1,000 Hz, more narrowly 150-400 Hz (e.g., about 200 Hz).

After the scanning for any given position is completed, the exciter may be repositioned (e.g., by incrementally rotating the carrier 180 about the axis 510 or translating the carrier along the axis 510). In this way, a composite profile of the subsurface properties of the entire ceiling mural may be maintained. A mechanism may be provided for holding the carrier 180 in a given orientation relative to the axis 510. In a simple embodiment, removable braces (not shown) may be formed for each of several orientations about the axis 510. Alternatively, an angular detent mechanism or selective locking mechanism may be provided. Depending upon the nature of surface irregularities, consistency of shape, or other parameters, it may be necessary to retune the cavity after each repositioning or otherwise as appropriate. It may also be appropriate to retract the exciter away from the mural prior to moving to the next position (e.g., by use of the jacks 190). Other carriers may be provided for other environments (e.g., a purely translatory carrier for a flat wall or ceiling).

Figure 7:
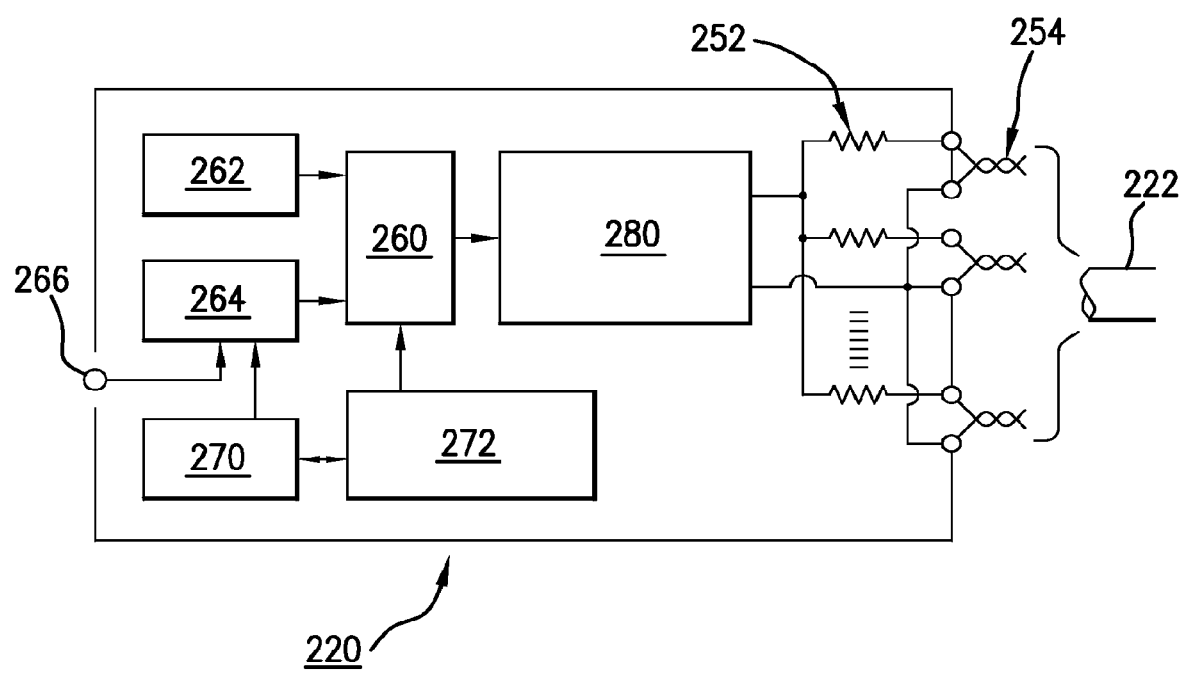
FIG. 7 is a schematic view of a driver of the exciter of FIG. 1.

FIG. 7 shows a simplified driver schematic of an exemplary driver 220. The driver includes a power amplifier 250 driving a plurality of power resistors 252 each connected in series with an associated one or more of the speakers 68 (e.g., through an associated twisted wire pair 254 assembled into the cable 222). Upstream of the amplifier 250 is a multiplier 260 receiving one input from an oscillator 262 and another input from a pulse generator 264. A short duration input to an input terminal 266 will initiate one pulse of the pulse generator 264. For example, a scanning control of the unit 200 may provide a next pulse signal. With non-scanning manual sensor positioning, the input may be from an operator-actuated button or other device. The exemplary driver 220 also includes an operator input program panel 270 and controller (e.g., computer or microcontroller) 272. The operator may program desired inputs to the panel 270 (e.g., desired oscillator frequency, desired pulse duration, and desired magnitude (e.g., in dB) of the sound level inside the cavity). The controller 272 may be programmed with an out-of-range override in case the entered values would produce a pulse that might potentially damage the exciter, associated hardware, or mural. Feedback (e.g., a warning light) may also be provided. This controller may also comprehend temporary conditions (e.g., a programmed operation that would be safe with a cool system may become unsafe once the speakers have reached a particular temperature). In the case of a projected overheating, the controller may thus temporarily disable the pulse generator 264.

Figure 8:
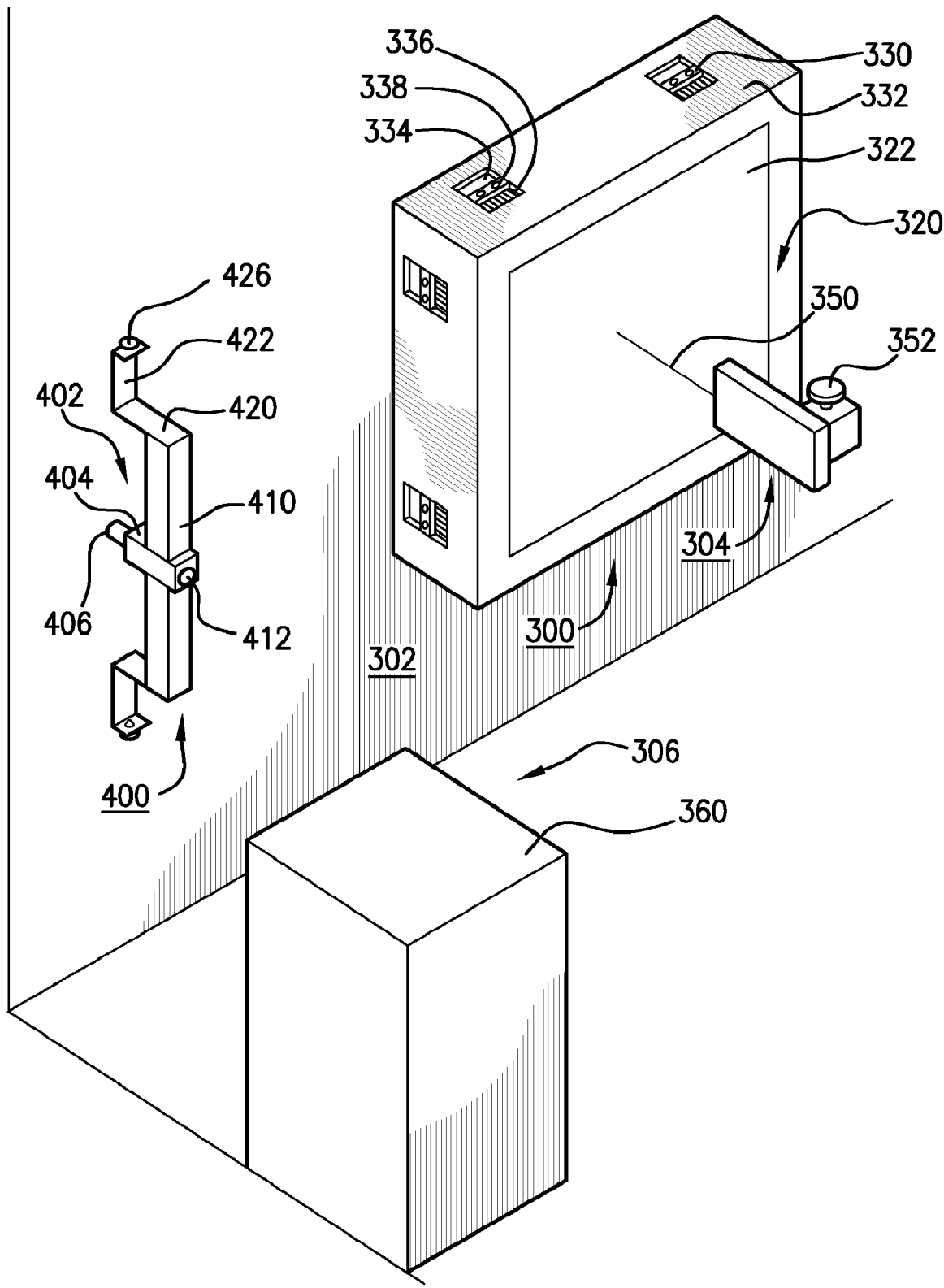
FIG. 8 is a view of an alternate exciter positioned for surveying a wall.

FIG. 8 shows an alternate exciter unit 300 positioned along a vertical wall surface 302. For ease of illustration, a support structure (if any) is not shown. FIG. 8 further shows a non-scanning laser generator/sensor unit 304. An exemplary unit 304 may be hand-held, tripod-mounted, or the like. FIG. 8 further shows a driver/control unit 306. For ease of illustration, power and control wiring to and between the various components or corresponding wireless communication pathways are not illustrated. As in the exemplary unit 20, the exemplary unit 300 includes a frame 320 and a forward window pane 322 cooperating to define a rearwardly-open cavity/chamber. The exemplary frame sides may be simply box-structured in cross-section, with speakers (not shown) mounted along the inboard wall. The pane 322 may be mounted to the top of these box sections or spanning between the inboard walls.

In place of the passageways 66 of the exciter 20, the exciter 300 has one or more tunable ports 330 in the outboard wall 332. Each of the exemplary ports 330 are formed by an associated aperture 334 and a movable shutter 336. The shutter 336 may be slidably mounted to the inboard surface of the associated outboard wall. The shutter 336 may be moved to determine the open cross-sectional area of the port 330. In an exemplary implementation, there is one port 330 associated with and immediately outboard of each loudspeaker. The open portion of each aperture 334 is shown near the fresco-facing side of the unit (bottom of the box section) to be relatively close to the gap for sound cancellation. The exemplary shutter 336 may be moved by a pair of spring-loaded finger-buttons 338. The buttons may be pressed toward each other (e.g., by operator thumbs and forefinger) to release from engagement with the lateral sides of the aperture 334. When released, the shutter may be slid toward or away from the mural side of the aperture 334 to provide area control. When the buttons are released, they engage the lateral sides to secure the shutter (e.g., by friction or detect action). Iterative tuning may be as described above.

The exemplary unit 304 emits a continuous non-scanning laser beam 350. The driver 306 may include a controller instrumentation panel 360 and other driver components (e.g., as discussed above). In operation, the operator manually directs the laser beam through the pane 322 to a particular location on the mural and then pushes the button 352. The button push provides a signal to the input terminal 266, causing the pulse generator 264 to cause the amplifier and loudspeakers to produce a sonic pulse. If the beam is aimed toward a substrate fault, the instrumentation panel 360 displays an indication of vibration at that location on the mural. More sophisticated displays may also be provided.

FIG. 8 also shows an alternate vibration detector unit 400 that may be used with an exciter unit as described above or otherwise. The exemplary unit 400 is a non-laser unit that may be representative of direct contact or other units. The exemplary unit 400 includes a geophone detector 402 having a housing 404 and a sensor foot 406. An exemplary foot 406 has a thin rubber or other elastomeric/resilient contact face for directly contacting the mural surface. The foot may be spring biased by biasing springs (not shown) to contact the mural with appropriate force. Exemplary geophone technologies are implemented in oil ground surveys. A geophone operates responsive to the relative movement of a steel sleeve and a coil, spring supported relative to the sleeve and within a field of a permanent magnet. A common geophone construction involves a short metallic (e.g., steel) cylindrical sleeve body concentrically carrying the permanent magnet spaced by non-magnetic material inwardly of end plates of the sleeve. The coil is positioned surrounding the magnet in the annular space between the magnet and cylinder and may be mounted to an inner sleeve held at both ends by spring disks for spring-biased centering reciprocation relative to the magnet. Vibration-induced relative motion between the inner and outer sleeves generates a voltage, BLV, where B is the flux density through the coil, in webers, L is the length of the coil wire, in meters, and V is the relative velocity, in meters per second. In the present use, the foot 406 may be mounted directly to one of the end plates.

The housing 402 forms a carriage slidable along a guide arm 410. The housing may be locked in position along the arm 410 by a set screw 412, detect mechanism, or other means. At each end of the arm 410, a thin leg wall (e.g., of sheet metal) 420 extends toward the mural. A thin foot wall 422 extends outward from the distal end of the leg wall 420 and is dimensioned to fit between the exciter foot/base and the mural (e.g., within the gap). A toe wall 424 extends back away from the mural and carries a set screw 426. The set screws may be used to mount the unit 400 to the exciter (e.g., by engaging the adjacent outboard wall surface of the exciter base with the outboard surface of the foot wall 422 contacting the adjacent base/foot section of the exciter.

With the exemplary unit 400, the exciter need not have a transparent pane. Advantageously, the pane (or an opaque replacement) may be formed as a door. The door may be openable to facilitate positioning of the geophone (e.g., by sliding the geophone along the arm 410 and/or moving the arm transversely (e.g., after loosening the screws 426). To facilitate such movement, the geophone may advantageously be provided with a retracting lever to retract the foot to avoid damaging the painting.

However, the mural sides of the sonic exciter feet and the foot walls 422 may be covered with resilient strips such as used for thermal insulation around doors and windows. In such a case, the sonic exciter may be pressed against the mural, and the counter-sound ports 330 closed, providing almost complete protection of the operator's ears from dangerous high intensity sound.

For initial surveys of very valuable murals to locate substrate failures, laser vibration sensors are preferred relative to contact sensors (e.g., press against the mural type vibration sensors, such as illustrated in the unit 400 of FIG. 9), because laser scanning over the mural is fast and safe, and because the contact of the geophone foot may cause damage. For the repair of a substrate fault, however, the surface must be repaired anyway. A contact vibration sensor may provide a simple in process evaluation of the substrate re-attachment process, at a low equipment cost.

One or more embodiments of the present invention have been described. Nevertheless, it will be understood that various modifications may be made without departing from the spirit and scope of the invention. Accordingly, other embodiments are within the scope of the following claims.

What is claimed is:

1. An apparatus for sonic excitation of a surface comprising:
    a transparent pane;
    a sidewall structure cooperating with the pane to define an open cavity facing the surface;
    at least one speaker positioned to introduce sound to the cavity; and
    sound canceling means for at least partially canceling transmission of the sound outside the cavity.

2. The apparatus of claim 1 wherein:
    the pane is nondestructively removable and replaceable; and
    the sound canceling means comprise at least one tunable passageway from a space within the sidewall structure behind the at least one speaker.

3. The apparatus of claim 2 wherein the tunable passageway is elongate along the sidewall structure and the sound canceling means includes means for simultaneously adjusting a sound collecting portion of the passageway and a throat of the passageway.

4. The apparatus of claim 1 wherein:
    the pane is essentially rectangular;
    the sidewall structure has four lengths, each length principally along an associated edge of the pane; and
    each length includes at least one of the speakers.

5. The apparatus of claim 1 further comprising:
    a plurality of removable adapter elements for accommodating the sidewall to different possible curvatures of the surface.

6. A system for determining a condition of a mural and substrate combination comprising:
   a laser positioned to direct a beam to a surface of the mural;
   a panel passing the laser;
   a sidewall structure cooperating with the pane to define an open cavity facing the surface; and
   a detector positioned to detect a return of the beam through the panel; and
   a processor coupled to the dectector and programmed by at lest one of hardware and software to analyze the return to determine the condition of the mural and substrate combination.

7. An apparatus for examination of a fresco mural comprising:
   a housing defining an open cavity facing the mural;
   a sound source positioned to introduce sound to the cavity; and
   a vibration detector positioned to detect vibrations of the mural induced by the sound.

8. The apparatus of claim 7 wherein:
   the vibration detector comprises a contact vibration sensor.

9. The apparatus of claim 7 wherein:
   the vibration detector comprises a laser generator and a light detector; and
   the housing comprises a pane essentially transparent to light from the laser generator.

10. The apparatus of claim 7 further comprising:
    a sound canceling system for at least partially canceling transmission of the sound outside the cavity.

11. A method for inspecting a mural and substrate combination comprising:
    providing a sound generating apparatus comprising:
      a transparent pane;
      a sidewall structure cooperating with the pane to define an open cavity; and
      a sound source positioned to introduce sound to the cavity
    positioning an open end of the cavity in proximity to the mural;
    generating sound from the sound source so as to excite the mural;
    directing a laser beam through the pane to the mural;
    detecting a return of the laser through the pane; and
    evaluating the return so as to determine a condition of the combination.

12. The method of claim 11 further comprising:
    directing a canceling sound from the sound source to an exterior of the sidewall structure to cancel a sound leakage from the cavity through a gap between the sidewall and the mural.

13. The method of claim 11 wherein:
    the sound is sequentially or progressively generated at a plurality of different frequencies.

14. The method of claim 11 wherein:
    the positioning is repeated for a plurality of positions;
    for each of the positions, the directing and detecting are repeated for a plurality of locations in a field of view through the pane; and
    the evaluating comprises determining at least one of:
      a transverse dimensional parameter of a void or adhesion failure;
      a depth of a void or adhesion failure; and
      a looseness of a piece of mural over a void or adhesion failure.

15. The method of claim 11 further comprising:
    selecting one or more adapters for matching curvature of the substrate so that along essentially the entirety of a cavity perimeter the sidewall structure is separated from the mural by a gap within a desired maximum extent.

16. The method of claim 11 wherein:
    the sound source comprises speakers within the sidewall structure; and
    the positioning positions the sidewall structure so that gaps between the sidewall structure and the combination do not exceed 5% of a height from the combination to the pane.

17. The method of claim 11 wherein:
    the combination forms a curved cylindrical ceiling surface; and
    the method further comprises installing shoes to the sidewall structure, the shoes having a shape corresponding to the shape of the curved cylindrical ceiling surface.

18. The method of claim 11 wherein:
    the sound source comprises a loudspeaker and an amplifier and the method further comprises:
      calculating an expected loudspeaker coil displacement, an expected resulting coil temperature, and an expected amplifier temperature and, if any of said expected loudspeaker coil displacement, expected resulting coil temperature, and expected amplifier temperature are excessive, preventing further sound from being generated.

19. The method of claim 18 wherein:
    calculation of the expected resulting coil temperature and the expected amplifier temperature is partially based upon calculated coil temperature and calculated amplifier temperature from prior operation.

20. The method of claim 11 wherein:
    said sound source is initially operated in a continuous, non-pulse operation; and
    said operation is terminated responsive to at least one of:
      a calculated expected loudspeaker coil displacement;
      a calculated expected coil temperature; and
      a calculated expected amplifier temperature, exceeding respective threshold values.

* * * * *